(12) United States Patent
Müller et al.

(10) Patent No.: US 9,316,571 B2
(45) Date of Patent: Apr. 19, 2016

(54) METHOD AND DEVICE FOR MONITORING THE STATE OF ROTOR BLADES

(71) Applicant: Technische Universität München, München (DE)

(72) Inventors: Mathias Müller, München (DE); Rolf Wojtech, München (DE); Thorbjörn Buck, München (DE)

(73) Assignee: Technische Universität München, München (DE)

( * ) Notice: Subject to any disclaimer, the term of this patent is extended or adjusted under 35 U.S.C. 154(b) by 0 days.

(21) Appl. No.: 14/427,087

(22) PCT Filed: Sep. 10, 2013

(86) PCT No.: PCT/EP2013/068705
§ 371 (c)(1),
(2) Date: Mar. 10, 2015

(87) PCT Pub. No.: WO2014/044575
PCT Pub. Date: Mar. 27, 2014

(65) Prior Publication Data
US 2015/0211969 A1    Jul. 30, 2015

(30) Foreign Application Priority Data
Sep. 18, 2012  (DE) .......................... 10 2012 108 776

(51) Int. Cl.
*G01N 3/20*  (2006.01)
*F03D 11/00* (2006.01)
(Continued)

(52) U.S. Cl.
CPC .............. *G01N 3/20* (2013.01); *F03D 11/0091* (2013.01); *G01M 11/083* (2013.01);
(Continued)

(58) Field of Classification Search
CPC .............. F03D 11/0091; F03D 7/0296; F05B 2260/80; F05B 2260/83; F05B 2270/332; F05B 2270/334; F05B 2270/807; F05B 2270/808; F05B 2270/821; G01M 11/083; G01M 15/14; G01M 5/0016; G01M 5/0041; G01N 3/20; G01P 15/093; Y02E 10/722

USPC ................ 73/660, 112.01, 495, 800, 862.192
See application file for complete search history.

(56) References Cited

U.S. PATENT DOCUMENTS

| | | | | |
|---|---|---|---|---|
| 8,511,177 B1 * | 8/2013 | Makaremi | ........... | G01M 5/0033 73/847 |
| 8,757,003 B1 * | 6/2014 | Makaremi | ........... | F03D 11/0091 73/847 |

(Continued)

FOREIGN PATENT DOCUMENTS

| | | |
|---|---|---|
| CN | 101460901 A | 6/2009 |
| CN | 101482448 A | 7/2009 |

(Continued)

OTHER PUBLICATIONS

Office Action, Germany Patent Application DE102012108776.8, 10 Pages, Date of Mailing Jun. 6, 2013.

(Continued)

*Primary Examiner* — Lisa Caputo
*Assistant Examiner* — Jonathan Dunlap
(74) *Attorney, Agent, or Firm* — Moser Taboada

(57) ABSTRACT

A method for state monitoring of a rotor blade of a wind turbine is described. The method comprises: measuring an acceleration of the rotor blade with a first signal, wherein the acceleration is measured at a first position at a predetermined distance from the rotor blade root in at least one direction comprising a first directional component orthogonal to the axis of the rotor blade, measuring a strain of the rotor blade with a second signal, wherein the strain is measured at a second position disposed in the area of the first position to the rotor blade root, determining a first positional change at the first position on the basis of the acceleration, determining a first value corresponding to the rotor blade stiffness or to the rotor blade elasticity by means of calculation on the basis of the first positional change and the strain, and determining the rotor blade state from the first value.

12 Claims, 5 Drawing Sheets

(51) Int. Cl.
- *G01M 11/08* (2006.01)
- *G01P 15/093* (2006.01)
- *G01M 5/00* (2006.01)
- *F03D 7/02* (2006.01)
- *G01M 15/14* (2006.01)
- *G01M 7/02* (2006.01)

(52) U.S. Cl.
CPC ............ *G01P 15/093* (2013.01); *F03D 7/0296* (2013.01); *F05B 2260/80* (2013.01); *F05B 2260/83* (2013.01); *F05B 2270/332* (2013.01); *F05B 2270/334* (2013.01); *F05B 2270/807* (2013.01); *F05B 2270/808* (2013.01); *F05B 2270/821* (2013.01); *G01M 5/0016* (2013.01); *G01M 5/0041* (2013.01); *G01M 7/025* (2013.01); *G01M 15/14* (2013.01); *Y02E 10/722* (2013.01)

(56) References Cited

U.S. PATENT DOCUMENTS

| | | | | |
|---|---|---|---|---|
| 8,820,149 | B2* | 9/2014 | Becker | G01M 15/14 73/112.01 |
| 2004/0057828 | A1 | 3/2004 | Bosche | |
| 2005/0276696 | A1 | 12/2005 | Lemieux | |
| 2009/0180875 | A1 | 7/2009 | Egedal et al. | |
| 2009/0246019 | A1 | 10/2009 | Volanthen et al. | |
| 2010/0135801 | A1* | 6/2010 | Melius | F03D 7/0224 416/44 |
| 2011/0041617 | A1* | 2/2011 | Cotrell | F03D 11/0091 73/660 |
| 2011/0265575 | A1* | 11/2011 | Koste | F03D 11/0033 73/660 |
| 2013/0255398 | A1* | 10/2013 | Philipsen | G01M 5/0016 73/800 |
| 2014/0020465 | A1* | 1/2014 | Laurberg | G01P 3/00 73/495 |
| 2015/0000404 | A1* | 1/2015 | Brenner | G01N 29/12 73/579 |

FOREIGN PATENT DOCUMENTS

| | | |
|---|---|---|
| CN | 102279018 A | 12/2011 |
| CN | 102330645 A | 1/2012 |
| CN | 102648345 A | 8/2012 |
| EP | 2112375 A2 | 10/2009 |
| WO | WO-2007131489 A1 | 11/2007 |
| WO | WO-2010046403 A2 | 4/2010 |

OTHER PUBLICATIONS

Search Report and Written Opinion, PCT/EP2013/068705, 10 Pages, Date of Mailing Jan. 7, 2014.

Written Opinion mailed Jan. 7, 2014 for PCT Application No. PCT/EP2013/068705.

* cited by examiner

METHOD AND DEVICE FOR MONITORING THE STATE OF ROTOR BLADES

TECHNICAL FIELD

The present invention relates generally to monitoring the operation of wind turbines, in particular to monitoring the state of a rotor blade of wind turbines. The invention relates in particular to an arrangement of fibre-optic sensors for determining the state of a rotor blade of a wind turbine.

PRIOR ART

In the field of monitoring of wind turbines, systems determining the state have gained in importance. The state of a rotor blade, e.g. wear, fatigue of material and other alterations stemming from aging or utilisation, is the subject of state monitoring of wind turbines. By knowing the state, maintenance can be scheduled, the current value of the facility can be estimated, and legislature-originated or customer-originated security obligations can be complied with.

In existing facilities, for example the state of the load cycles is estimated, wherein the number of strain cycles, blade rotations, i.e. gravitational load cycles, or gusts of wind are acquired. Cycles may be determined in time intervals, e.g. 10 minutes, on the basis of the maximum load values in the time intervals, and the state can be estimated on the basis of the number of cycles having a certain load.

For example, FIG. 1 depicts the graph 13: This graph illustrates the stiffness of a rotor blade plotted along the axis 11 as a function of the number of load cycles or as a function of time at the axis 12. Within a relatively short period of time after startup operations, the stiffness decreases at first, in order to remain, within the dependence of further parameters like temperature and air moisture, approximately constant for the regular operation state. When the state of a rotor blade has reached a critical value, i.e. if an excessive aging, load or the like has occurred, the stiffness decreases, wherein shortly afterwards a failure of material may occur. The state of the decrease of stiffness is depicted in the area between auxiliary lines 20 and 22, wherein beginning with auxiliary line 22, a failure of material may occur.

Document US 2009/180875 A1 discloses a method for determining the material fatigue stress of a wind turbine and for controlling the material fatigue stress, as well as corresponding wind turbines. The method for determining the material fatigue stress of a wind turbine in operation comprises providing a transfer function which links a measured value of a first sensor to a measured value of a second sensor. The first and the second measured values are obtained using a reference wind turbine having the first and the second sensors mounted thereto. A third sensor is mounted to the wind turbine in operation and corresponds, with respect to its type and the location of mounting, to the first sensor. By making use of the transfer function, a transfer function value is calculated which corresponds to a measured value obtained from the third sensor. Then, the material fatigue stress of the wind turbine in operation is calculated on the basis of the calculated transfer function value.

SUMMARY OF THE INVENTION

The present invention provides a method for state monitoring of a rotor blade according to claim 1. Furthermore, the present invention provides a device adapted for state monitoring of a rotor blade of a wind turbine according to claim 8.

According to an embodiment, a method for monitoring the state of a rotor blade of a wind turbine is provided. The method comprises: measuring an acceleration of the rotor blade with a first signal, wherein the acceleration is measured at a first radial position at a predetermined distance from the rotor blade root in at least one direction comprising a first directional component orthogonal to the axis of the rotor blade; measuring a strain of the rotor blade with a second signal, wherein the strain is measured at a second radial position disposed in the area of the first radial position to the rotor blade root; determining a first positional change at the first radial position on the basis of the acceleration; determining a first value corresponding to the rotor blade stiffness or to the rotor blade elasticity by means of calculation on the basis of the first positional change and the strain, and determining the rotor blade state from the first value.

According to another embodiment, a device adapted for monitoring the state of a rotor blade of a wind turbine is provided. The device comprises: at least one acceleration sensor adapted for measuring an acceleration of the rotor blade, wherein the acceleration is measured in at least one direction comprising a first directional component orthogonal to the axis of the rotor blade; at least one strain sensor adapted for measuring a strain of the rotor blade with a second signal, wherein the strain is measured at a second radial position disposed in the area of a first radial position of the acceleration sensor to the rotor blade root; and an evaluation unit connected to the at least one acceleration sensor for receiving a first signal from the acceleration sensor and connected to the at least one strain sensor for receiving a second signal from the strain sensor; and wherein the reception of the first signal from the first radial position is conducted at a predetermined distance from the rotor blade root; wherein the evaluation unit is adapted to determine a first positional change at the first radial position on the basis of the first signal of the acceleration sensor; and wherein the evaluation unit is adapted to determine a first value corresponding to the rotor blade stiffness or to the rotor blade elasticity by means of calculation on the basis of the first positional change and the second signal.

BRIEF DESCRIPTION OF THE DRAWINGS

Embodiments are depicted in the drawings and described in detail in the following description. In the drawings.

Figure 1:
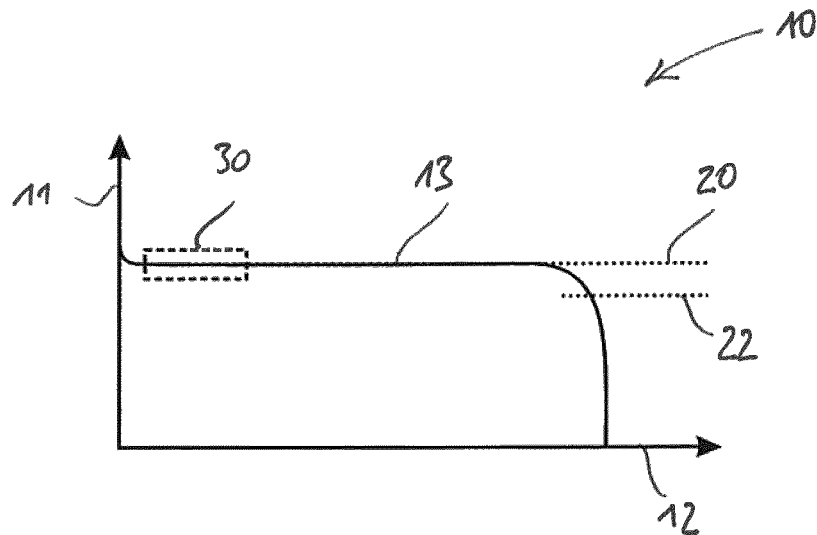
FIGS. 1 and 2 show graphs for illustrating the dependence of the stiffness or of an analog quantity or of a corresponding value, respectively, from the state of a rotor blade and further parameters, and they illustrate the information used in the embodiments of the invention.

In the drawings, like reference signs indicate like or functionally equivalent components or steps.

MODES FOR CARRYING OUT THE INVENTION

In the following, detailed reference is made to different embodiments of the invention, wherein one or more examples are illustrated in the drawings.

According to embodiments of the invention, in order to monitor or to determine a state of a rotor blade, a strain sensor, in particular an athermal strain sensor is employed, combined with one or more acceleration sensors. According to typical embodiments, fibre-optic acceleration sensors and fibre-optic sensors are employed.

One or more acceleration sensors can be mounted, for example, approximately at half the radius along the length of the rotor blade. Using the acceleration signal from the sensor, the shift or the distortion, respectively, of the blade can be calculated by way of integration. Strain sensors can be mounted in the blade root. Using the signals from the strain sensors, the bending moment applied to the blade can be calculated. The quotient of the bending moment and the shift is proportional to the stiffness of the rotor blade. The stiffness of the construction material of the rotor blade can be regarded as a quantity for the state or the strength of the construction material of the rotor, respectively. Here, the strength decreases if single fibers of a fiber composite material rupture, or if the lamination of the fibers delaminates. Thus, an in-situ measurement of the blade state may be performed with the described arrangements and methods. Here, the in-situ measurement allows for an improved detection of aging, fatigue of material and similar critical states when compared to an estimation of the number of the load cycles.

FIG. 1 depicts a graph 10. In the curve 13, the stiffness is plotted on the axis 11 as a function of time or of the number of load cycles, respectively. Here, the axis 12 corresponds to the time or to the number of load cycles, respectively. As shown in curve 13, at the beginning of the employment of a rotor blade, first the stiffness decreases, in order to remain constant over a longer period of time. This constant value is indicated by an auxiliary line 20. At the end of the life span of a rotor blade, the stiffness decreases relatively notably. As outlined above, this may be caused by rupture of single fibers in the fiber composite material or by delamination of the lamination with the fibers. The decrease of the stiffness from approximately 10% to 20%, indicated by the auxiliary line 22, typically induces the disruption of the rotor blade. In order to provide for a secure operation of the wind turbine, this has to be identified in good time.

Figure 2:
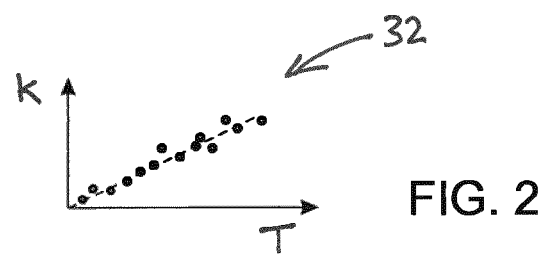

The measurement arrangement and the measurement method with sensors, typically fibre-optic sensors, according to embodiments of the present invention allows for a accuracy of measurement within the range of about 1%, which is sufficient for identifying the decrease at the end of the life span. However, also effects like temperature and moisture cause fluctuations within the range of 1%. This is depicted in FIG. 2. Here, the graph 32 illustrates the stiffness as a function of temperature. Herein, the temperature is illustrated exemplarily, and a similar dependency can also be illustrated for moisture and further effects. According to typical embodiments of the present invention, in the measurement methods, the dependency on temperature, moisture and/or further parameters is determined in a learning period. This learning period is indicated by a region 30 in FIG. 1. With the learning period at the beginning of the employment of the rotor blade, the influence of the parameters, such as temperature, air moisture and the like, can be determined. Thereby, the influence of those quantities can be taken into account at the subsequent measurement operation, such that fluctuations of the stiffness based on these quantities do not lead to a uncertainty of measurement.

According to further embodiments, which can be combined with other embodiments described herein, an averaging of the measurement values over a plurality of hours up to a plurality of days may be performed, since the state of a rotor blade of a wind turbine only changes slowly. An averaging may be performed, for example, over 1 hour up to 5 days, in particular over 12 hours up to 3 days.

Figure 3:
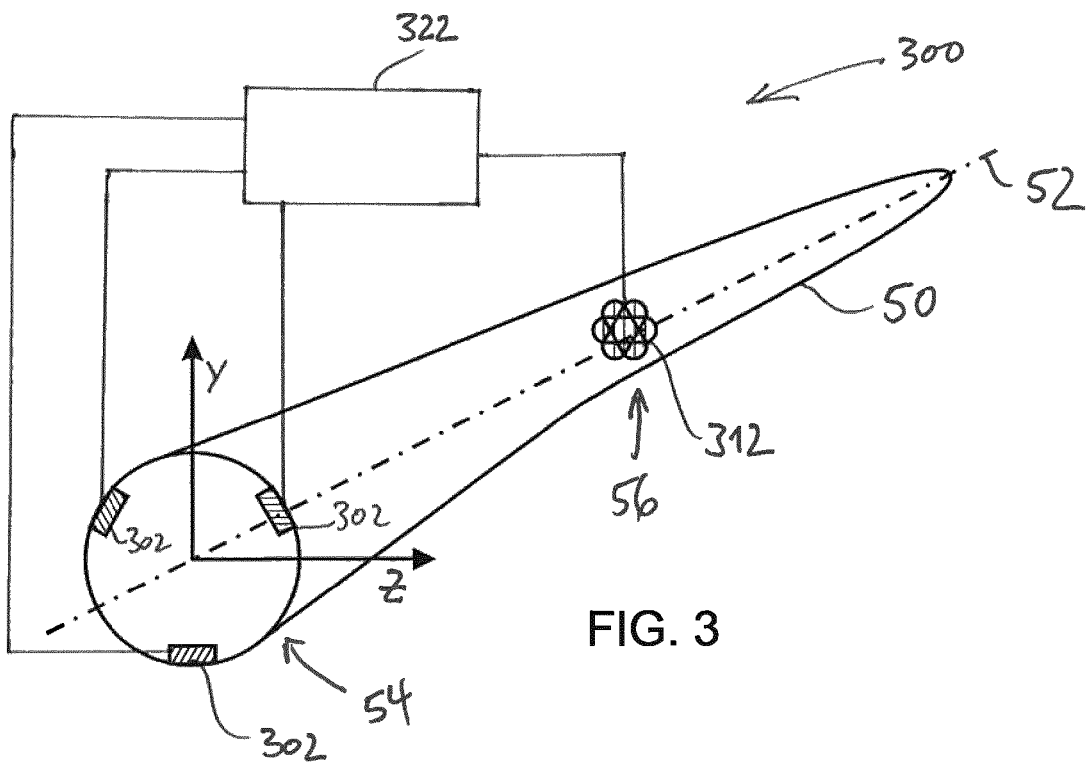
FIG. 3 schematically depicts a rotor blade with an arrangement or a device, respectively, adapted for state monitoring of a rotor blade of a wind turbine according to the embodiments described herein.

FIG. 3 depicts a rotor blade 50 of a wind turbine. The rotor blade 50 comprises an axis 52 and a coordinate system aligned thereto, i.e. a blade-fixed coordinate system illustrated exemplarily in FIG. 3 by the y-axis and the z-axis. The rotor blade 50 of FIG. 3 is provided with an arrangement 300 for state monitoring of the rotor blade. The arrangement 300 of FIG. 3 comprises 3 (three) strain sensors 302 and an acceleration sensor 312. The strain sensors and the acceleration sensor are connected to an evaluation unit 322. The strain sensors 302 are mounted at the blade root 54 of the rotor blade 50. The acceleration sensor 312 is mounted at a position 56 which is situated approximately at half the length of the rotor blade 50. According to typical embodiments, the strain sensor or the strain sensors may be mounted at an axial distance to the blade root of 5 meters or less. According to further typical embodiments, which can be combined with other embodiments described herein, the acceleration sensor or the acceleration sensors can be mounted within a range of ±5 meters in axial direction from the blade center. Here, the axial distance or the axial direction, respectively, refer to the longitudinal axis 52 of the rotor blade 50. According to further embodiments, the acceleration sensor or the acceleration sensors can be mounted within a range from the center of the rotor blade in the direction of the tip of the rotor blade.

By means of the strain sensors 302, the bending moment applied to the blade can be determined. According to embodiments of the present invention, at least one strain sensor 302 is employed, such that the bending moment can be determined in one direction. According to further typical embodiments, at least 3 (three) strain sensors 302 or at least 4 (four) strain sensors 302 can be employed, respectively, in order to determine a bending moment within the y-z plane of the coordinate system depicted in FIG. 3. With an appropriate arrangement of 2 (two) strain sensors, e.g. at different angular coordinates of the blade root, the bending moments, applied on the rotor blade in 2 (two) directions, typically 2 (two) orthogonal directions, can also be measured by employing 2 (two) sensors. For this purpose, the 2 (two) sensors are typically mounted with their angular coordinates turned by 90°, or mounted with their angular coordinates not turned by 180°, respectively.

Figure 9A:
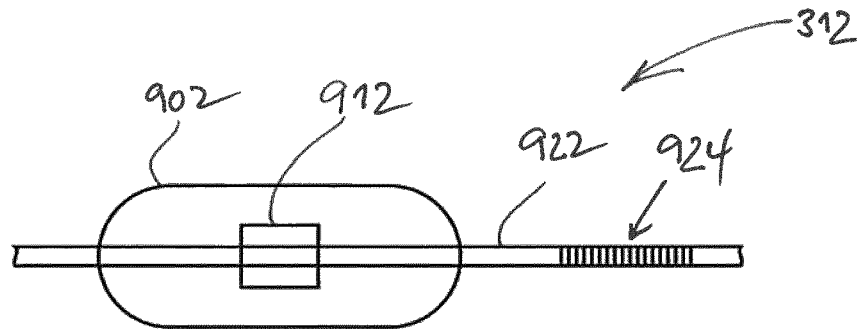
FIGS. 9A and 9B schematically depict acceleration sensors for employment in the embodiments described herein.
Figure 9B:
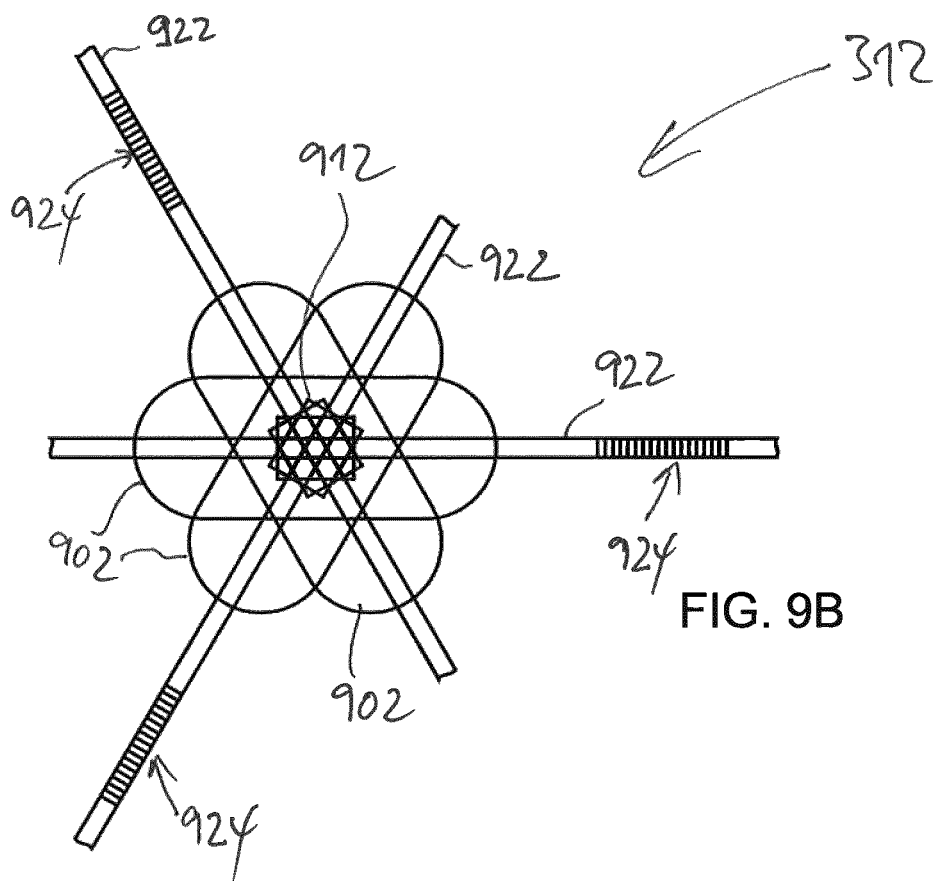

The acceleration sensor 312, which is described later with reference to FIGS. 9A and 9B, includes a mass, the acceleration of which is measured in the sensor. According to typical embodiments, the employed strain sensors and/or the employed acceleration sensors may be fibre-optic sensors. Here, the strain or the acceleration of the mass, respectively, is measured optically by fiber Bragg gratings in a fiber. By employing these sensors, the measurement accuracy described above may be provided. Further, those sensors provide advantageous properties for the employment in wind turbines.

Figure 4:
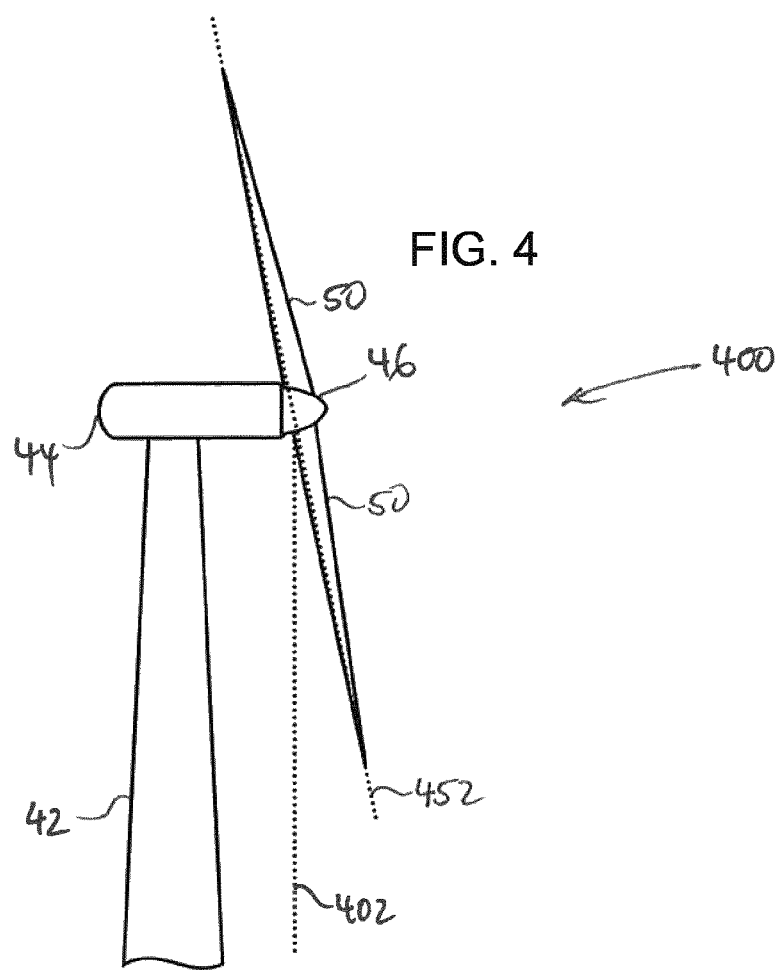
FIGS. 4 and 5 depict a wind turbine and a rotor for illustrating the transformations of signals and values used in the embodiments.
Figure 5:
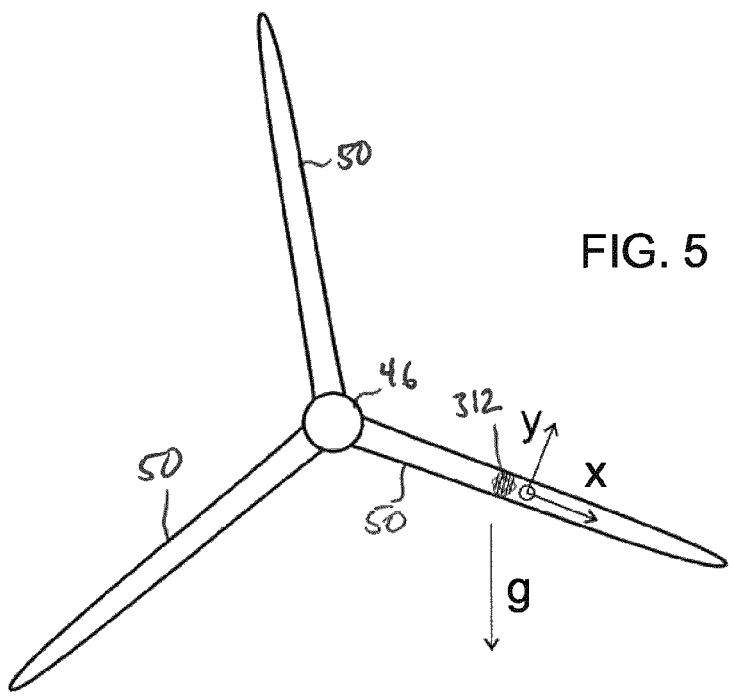

The employment of the sensors 302 and 312 or their arrangement with respect to another, respectively, and the cooperation of the evaluation unit 322 for monitoring a state of a rotor blade will be explained in more detail with reference on FIGS. 4 and 5 or with reference to the signals and values illustrated in FIGS. 6 and 7, respectively. FIG. 4 depicts a part of a wind turbine 400. A nacelle 44 is disposed on a tower 42. Rotor blades 50 are disposed at a rotor hub 46, such that the rotor (including the rotor hub and the rotor blades) rotates within a plane depicted by a line 452. Typically, this plane is inclined relatively to the vertical line 402. FIG. 5 illustrates a front view of the rotor blades 50 and the rotor hub 46 in the direction of the rotor axis, wherein the coordinates x and y in the blade-fixed coordinate system, the gravitational force or gravitational acceleration g, respectively, and the sensor 312 are shown.

Figure 6:
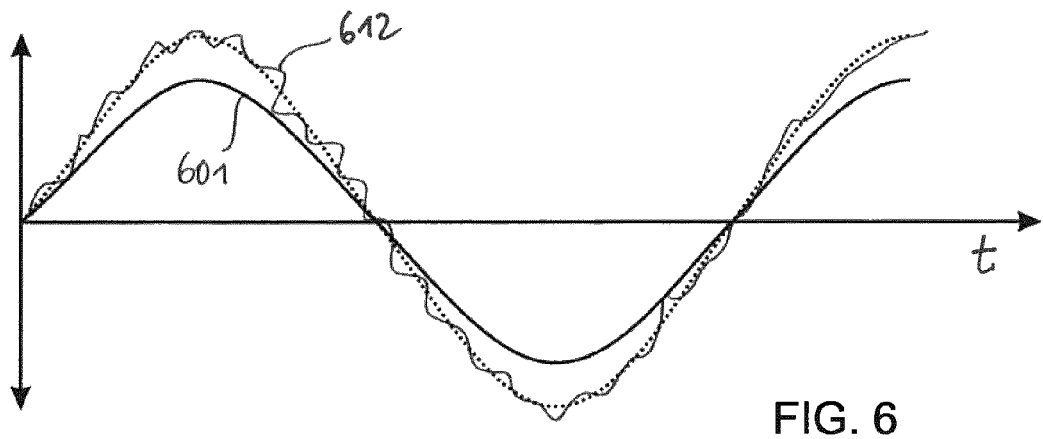
FIG. 6 schematically depicts an exemplary progression of an acceleration signal.
Figure 7:
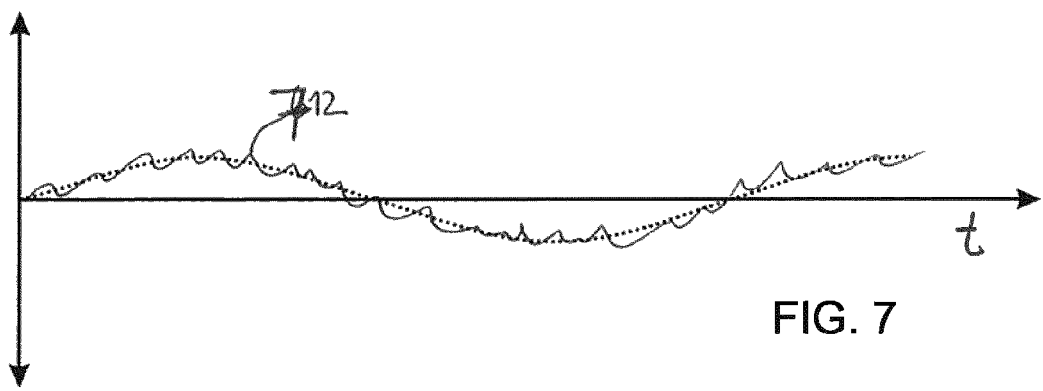
FIG. 7 schematically depicts a corresponding evaluation of the signal of FIG. 6.

Upon a rotation of the rotor of the wind turbine, the acceleration sensor 312 measures, among others, the gravitational acceleration g, which is indicated by a curve 601 in FIG. 6. This gravitational acceleration is measured, in the coordinate system according to FIG. 5, in the y-direction and in the x-direction. Due to the inclination of the rotor, which is depicted in FIG. 4, in the coordinate system of FIG. 5, a signal is also superimposed with the gravitational acceleration in the z-direction to a certain extent. The gravitational signal is superimposed with the measurement signal 612 depicted in FIG. 6, which is typically measured in the y-direction depicted in FIG. 5. By eliminating the gravitational signal in the measurement signal, the signal 712 illustrated in FIG. 7 is obtained.

Controllers of modern wind turbines typically include a so-called pitch control, wherein the rotor blade is turned among the axis 52 depicted in FIG. 3. Accordingly, in a blade-fixed coordinate system, the y-direction depicted in FIG. 5 changes during a rotation of the rotor blade 50 around the axis 52.

When considering the acceleration measured by an acceleration sensor 312, which includes the influence of the gravitational acceleration on a mass, a consideration of the different coordinate systems is necessary in order to improve the interpretation of the signals. On the one hand, there is a blade-fixed coordinate system. This is depicted in FIG. 3. Upon rotation of the rotor blade about the axis 52, the coordinate system, as well as the sensors 302 and the sensor 312, rotate. Furthermore, there is a coordinate system which is fixed with respect to the rotor hub 46. This is a rotating coordinate system which can be employed independently of a pitch control. Furthermore, there is a stationary coordinate system which is fixed relative to the wind turbine 400. Hence, it is fixed relative to the gravitational force or gravitational acceleration, respectively.

In typical embodiments, for a correction of the signal or the signals of the acceleration sensor and/or the strain sensors, i.e. of a signal in the x-direction, the y-direction and the z-direction in the blade-fixed coordinate system, a transformation into the stationary coordinate system is performed, wherein the rotation of the rotor, the pitch angle of the rotor blade, and the inclination of the rotor, illustrated by the lines 452 and 402 in FIG. 4, are taken into account. In the stationary coordinate system, the gravitational acceleration can be removed from the signal. Thereafter, an inverse transformation can be performed into the coordinate system which is fixed with respect to the rotor hub. In this coordinate system, which is fixed relative to the rotor hub, an acceleration is typically determined which is substantially in parallel to the direction of the wind or substantially in parallel to the rotational axis of the rotor, which is denoted as $\tilde{z}$ hereinafter, and an acceleration $\tilde{y}$ is determined which is orthogonal to $\tilde{z}$ and corresponds substantially to the tangential velocity of the rotor blade. In many relevant applications, an acceleration along the x-direction depicted in FIG. 5 or a direction $\tilde{x}$, respectively, is negligible for the evaluation.

According to typical embodiments, the signal or the signals corresponding to an acceleration are integrated over time, particularly integrated twice over time, in order to determine a shift, a change of the position or a change of the location of the acceleration sensor and thereby a corresponding shift or a corresponding change of the location of the rotor blade position. Here, the acceleration sensor is assigned a location on the rotor blade. The sensor measures the acceleration at this location of the rotor blade. This acceleration is obtained from the gravitational acceleration, from the rotation of the rotor, and from movement, i.e. deformation (strain) of the rotor blade. By integrating the signal (twice) over time, the shift of this location or the positional change of this location is obtained, respectively. The shift of this location within the meaning of a vector shift of the positional coordinate of this location and the positional change of this location within the meaning of new positional coordinates x', y' and z' by the relationship $x'=x+\Delta x$, $y'=y+\Delta y$, and $z'=z+\Delta z$, wherein the vector ($\Delta x$, $\Delta y$, $\Delta z$) denotes the positional change, are used synonymously herein.

Upon the application of a predetermined force or upon the effect of a specific moment, the strain, i.e. a shift or a positional change, is proportionally related thereto by the modulus of elasticity or by the bending stiffness, respectively. With the help of the strain sensors 302 depicted in FIG. 3, the bending moment applied to the blade can be determined. Thus, a quantity for the stiffness or the elasticity of the rotor blade can bei determined on the basis of the value of the shift or the value of the positional change and the value of the bending moment, respectively. Here, the quotient of the bending moment and the shift, i.e. the bending moments caused by the shift, is proportional to the stiffness. According to embodiments of the present invention, which can be combined with other embodiments, this value is used for state monitoring of a rotor blade in a wind turbine according to the relationship illustrated in FIG. 1.

According to embodiments of the invention, the acceleration is measured in at least one direction, preferably in the above-described direction, which is substantially parallel to the tangential velocity of the rotor blade. With a known pitch angle for regular operation, i.e. a typical or commonly occurring pitch position, this can be provided by accordingly mounting a one-dimensional acceleration sensor in the rotor blade, i.e. in the blade-fixed coordinate system. A bending moment in the corresponding or applicable direction, i.e. in the parallel direction, can also be provided by appropriate mounting of a strain sensor 302. Thus, according to embodiments of the present invention, a state monitoring using a one-dimensional acceleration sensor and a strain sensor can be performed. However, according to typical embodiments, an acceleration is measured in 3 (three) directions, and a strain or a bending moment, respectively, is determined by at least 2 (two) strain sensors along an arbitrary orientation within the plane of the blade root. Thereby, a monitoring can be performed independently from the pitch angle or along multiple coordinates in any desired coordinate system. The calculation along multiple coordinates may result in a more reliable state monitoring. Moreover, if typical orientations of the wear or damage of the rotor blades are known, in particular these directions can be monitored.

FIG. 6 illustrates a typical example of a signal of the acceleration sensor or the acceleration sensors in the direction of ỹ, i.e. in a coordinate system which is fixed relative to the rotor hub. After a correction of the influence of the gravitation (601 in FIG. 6), a value 712 is obtained, as illustrated in FIG. 7. This progression can be integrated twice over time in order to measure the shift of the rotor blade at the position which corresponds to the position of the acceleration sensor. The sinusoidal progression illustrated by the dotted line in FIG. 7 corresponds to a positional change of the position in the rotor blade which is caused by the gravitational acceleration exerted on the mass of the rotor blade. In other words: The rotor blade bends due to its self-weight.

Figure 8:
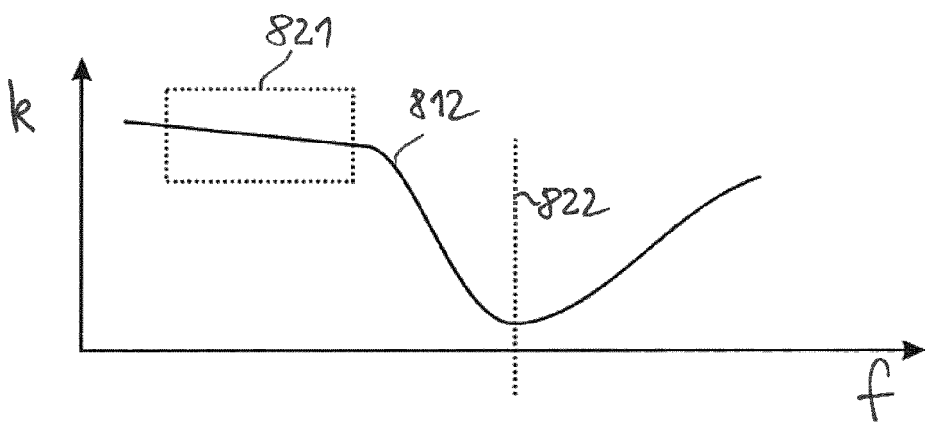
FIG. 8 schematically depicts another evaluation of the signal of FIG. 6.

Signals of the acceleration sensor or the acceleration sensors in the x̃ direction, i.e. parallel to the rotational axis of the rotor, typically show dynamic characteristics with high frequency components which are caused, for example, by gusts of wind. Typically, the acceleration signals can be filtered by their frequency components, wherein, for example, a low-pass filter can be employed. FIG. 8 illustrates a Fourier transform, wherein the stiffness k is plotted over the frequency f. The curve 812 exposes a typical progression having a quasi-statical area 821 and a natural frequency 822. Here, according to typical embodiments, a low-pass filter for frequencies of 0.6 Hz or below, typically 0.4 Hz or below, can be applied to the signals or values of the sensors. At a rotational speed of, for example, 0.2 Hz, this filtering results in an essentially smooth sinusoidal progression for the signal depicted in FIG. 7.

According to further typical embodiments, signals within the range of the natural frequency 822 can be used. The natural frequency is, for example, within the range of 0.8 Hz to 1.2 Hz. Within the range of the natural frequency, the rotor blade undergoes greater positional deviations, which may result in a better measurement accuracy. Since the evaluation of the signals is more difficult due to the more complex characteristics of the rotor blade, according to a preferred embodiment, an evaluation may be performed with a low-pass filter and a band-pass filter in the vicinity of the natural frequency and separate from each other. By the evaluation in both frequency ranges, i.e. by an additional evaluation within the range of the natural frequency, additional information may be used and thus, an improved measurement accuracy can be achieved.

The acceleration sensors 312 used in the arrangement and method described herein will now be described with reference to FIGS. 9A and 9B. FIG. 9A illustrates an acceleration sensor 312, wherein a mass 912 is mounted on an optical fiber. A housing 902 is designed such that upon an acceleration of the mass 912, a strain occurs, i.e. a relative change of length (elongation or contraction) of the optical fiber 922. As a result of the strain of the fiber 922, the fiber Bragg grating 924 is changed. This results in a modified reflection or transmission of the fiber Bragg grating, respectively, with respect to the respective reflected or transported wave lengths. This change can be used as a quantity of the strain of the fiber and, therefore, indirectly as a quantity of the acceleration of the mass 912. An acceleration sensor 312 is shown in FIG. 9B. In this arrangement, 3 (three) of the sensors shown in FIG. 9A are combined, wherein the rotation of the sensors in the illustration are meant to show a three-dimensional arrangement. Thus, 3 (three) acceleration sensor are measured within one coordinate system, e.g. within a cartesian coordinate system.

Figure 10:
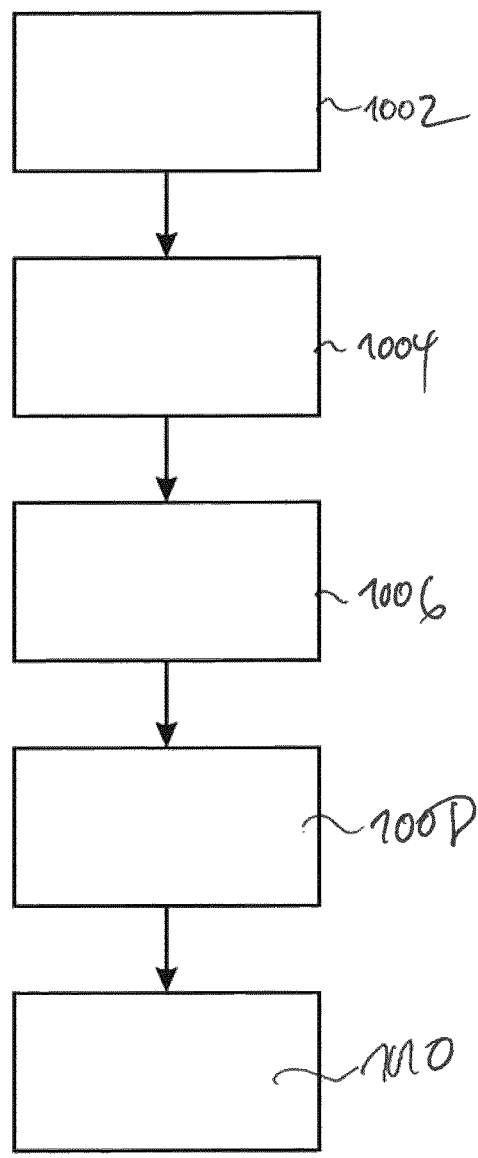
FIG. 10 depicts a flowchart of a method for monitoring the state of a rotor blade of a wind turbine according to embodiments of the invention.

FIG. 10 illustrates a flowchart of a method for state monitoring of a rotor blade of a wind turbine according to embodiments described herein. In step 1002, an acceleration of the rotor blade is measured using a first signal. Here, at least one directional component perpendicular to the axis of the rotor blade is measured. In step 1004, a strain is measured using a second signal. From the first signal for the acceleration, a positional change of the acceleration sensor is determined in step 1006, the positional change corresponding to a positional change of the respective rotor blade position. By calculation using the positional change and the strain, a quantity for the stiffness of the rotor blade or for the elasticity of the rotor blade is obtained in step 1008. This quantity is used in step 1010 for monitoring the rotor blade state.

According to typical embodiments, an integration twice over time is used in order to determine the positional change at the location of the acceleration sensor. Typically, the acceleration is measured in 3 (three) directions, e.g. directions of a Cartesian coordinate system, and the strain is measured in at least 2 (two) directions, such that a strain with an arbitrary orientation within the plane of the blade root may be determined. Further, for the state monitoring, an averaging over a time period of 1 (one) hour or longer may be performed, in particular an averaging over a time period of one day or longer. Thereby, the measurement accuracy is improved, and the state of the rotor blade can be determined sufficiently, i.e. in good time. According to further typical embodiments, which can be combined with other embodiments described herein, for the measurement of the acceleration or the strain, fibre-optic sensors are used, wherein particularly sensors having a fiber Bragg grating can be employed. For example, fibre-optic acceleration sensors combined with fibre-optic strain sensors are used. Typically, for embodiments of the arrangement and methods described herein, a strain sensor at the blade root or in the vicinity thereof, and an acceleration sensor with an axial distance to the blade root of at least half of the blade radius are used.

Although the present invention has been described on the basis of typical embodiments, the present invention is not limited thereto, and may be modified in various different ways. In addition, the invention is not limited to the possible applications mentioned.

The invention claimed is:

1. Method for monitoring the state of a rotor blade of a wind turbine, comprising:
    measuring an acceleration of the rotor blade with a first signal, wherein the acceleration is measured at a first radial position at a predetermined distance from the rotor blade root in at least one direction comprising a first directional component orthogonal to the axis of the rotor blade;
    measuring a strain of the rotor blade with a second signal, wherein the strain is measured at a second radial position disposed in the area of the first radial position to the rotor blade root;
    determining a first positional change on the basis of the acceleration;
    determining a first value corresponding to the rotor blade stiffness by means of calculation on the basis of the first positional change and the strain; and
    determining the rotor blade state from the first value.

2. The method of claim 1, wherein, for determining said first positional change, the signal of the acceleration is integrated over time.

3. The method of claim 1, wherein the acceleration is measured in three directions, and wherein the strain is measured in order to measure bending moments in two directions.

4. The method of claim 3, wherein the strain is measured in two orthogonal directions.

5. The method of claim 1, wherein, for determining the rotor blade state, said first value is averaged.

6. The method of claim 5, wherein said first value is averaged over a time period of 1 hour or longer.

7. The method of claim 1, wherein the acceleration is measured by means of a fiber-optic acceleration sensor and/or wherein the strain is measured by means of a fiber-optic strain sensor.

8. The method of claim 1, wherein the first radial position is located approximately at half the blade radius or in between half the blade radius and a rotor blade (tip and/or wherein the second radial position is located at a distance of 5 meters or less from the blade root.

9. The method of claim 1, wherein for determining said first value, a coordinate transformation into a coordinate system of said wind turbine and/or into a coordinate system of the rotor hub is performed.

10. Device for monitoring the state of a rotor blade of a wind turbine, comprising:
    at least one acceleration sensor adapted to measure an acceleration of the rotor blade, wherein the acceleration is measured in at least one direction comprising a first directional component orthogonal to the axis of the rotor blade;
    at least one strain sensor adapted to measure of a strain of the rotor blade with a second signal, wherein the strain is measured at a second radial position disposed in the area of a first radial position of the acceleration sensor to the rotor blade root;
    an evaluation unit connected to the at least one acceleration sensor for receiving a first signal from the acceleration sensor and connected to the at least one strain sensor for receiving a second signal from the strain sensor, and wherein the reception of the first signal is performed from the first radial position at a predetermined distance from the rotor blade root;
    wherein the evaluation unit is adapted to determine a first positional change at the first radial position on the basis of the first signal of the acceleration sensor;
    wherein the evaluation unit is adapted to determine a first value corresponding to the rotor blade stiffness by means of calculation on the basis of the first positional change and the second signal.

11. The device according to claim 10, wherein the at least one acceleration sensor is a fibre-optic sensor, and/or wherein the at least one strain sensor is a fibre-optic strain sensor.

12. The device of claim 10, wherein the first radial position is located within the range of half the blade radius to the blade tip and/or wherein the second radial position is located at a distance of 5 meters or less from the blade root.

* * * * *